(12) United States Patent
Murthy et al.

(10) Patent No.: US 8,188,300 B2
(45) Date of Patent: *May 29, 2012

(54) ATORVASTATIN CALCIUM PROPYLENE GLYCOL SOLVATES

(75) Inventors: K.S. Keshava Murthy, Ancaster (CA); Yajun Zhao, Brantford (CA); Allan W. Rey, Brantford (CA); Daqing Che, Brantford (CA); David A. Stradiotto, Brantford (CA); Uma Kotipalli, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/946,183

(22) Filed: Nov. 15, 2010

(65) Prior Publication Data

US 2011/0065931 A1    Mar. 17, 2011

Related U.S. Application Data

(62) Division of application No. 11/808,942, filed on Jun. 14, 2007, now Pat. No. 7,834,195.

(60) Provisional application No. 60/897,106, filed on Jan. 24, 2007.

(51) Int. Cl.
*C07D 207/00* (2006.01)
(52) U.S. Cl. ....................................... 548/537
(58) Field of Classification Search .................... 548/537
See application file for complete search history.

(56) References Cited

U.S. PATENT DOCUMENTS

| | | |
|---|---|---|
| 3,970,651 A | 7/1976 | Kaplan et al. |
| 4,091,213 A | 5/1978 | Kaplan et al. |
| 4,681,893 A | 7/1987 | Roth |
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,397,792 A | 3/1995 | Butler et al. |
| 5,969,156 A | 10/1999 | Briggs et al. |
| 6,274,740 B1 | 8/2001 | Lin et al. |
| 6,605,729 B1 | 8/2003 | Byrn et al. |
| 6,977,243 B2 | 12/2005 | Li et al. |
| 6,992,194 B2 | 1/2006 | Lidor-Hadas et al. |
| 7,105,179 B2 | 9/2006 | Li et al. |
| 7,112,604 B2 | 9/2006 | Wang et al. |
| 7,834,195 B2 * | 11/2010 | Murthy et al. ................ 548/537 |
| 2004/0019211 A1 | 1/2004 | Remenar et al. |
| 2005/0004206 A1 | 1/2005 | Aronhime et al. |
| 2005/0106243 A1 | 5/2005 | Doser et al. |
| 2005/0267302 A1 | 12/2005 | Barton et al. |
| 2006/0052432 A1 | 3/2006 | Remenar et al. |
| 2006/0199855 A1 | 9/2006 | Murthy et al. |
| 2006/0223794 A1 | 10/2006 | Mourghol Hickey et al. |

FOREIGN PATENT DOCUMENTS

| | | |
|---|---|---|
| CA | 1101840 | 5/1981 |
| JP | 10581375 | 8/1975 |
| JP | 01290682 | 11/1989 |
| WO | WO 9703959 | 2/1997 |
| WO | WO 9703960 | 2/1997 |
| WO | WO 0071116 | 11/2000 |
| WO | WO 03078379 | 9/2003 |
| WO | WO 2004060347 | 7/2004 |
| WO | WO 2006012499 | 2/2006 |

OTHER PUBLICATIONS

Shen et al. (J. Pharm. Pharmacol. Sep. 2006; 58(9): p. 1183-1191).*
Hurley, et al., "Photodecomposition of CI-981, an HMG-CoA Reductase Inhibitor", Tetrahedron, vol. 49(10), pp. 1979-1984 (1993).
Toda, R., "Isolation and Oprical Resolution of Materials Utilizing Inclusion Crystallization", Topics in Curr. Chem. vol. 140, pp. 43-69 (1987).

* cited by examiner

*Primary Examiner* — Andrew D Kosar
*Assistant Examiner* — Valerie Rodriguez-Garcia

(57) ABSTRACT

Atorvastatin calcium propylene glycol solvates and processes to prepare these novel solvates which are particularly useful and suitable for pharmaceutical applications.

22 Claims, 16 Drawing Sheets

DSC Thermogram of Atorvastatin Calcium Propylene Glycol Solvate prepared from Racemic Propylene glycol IR (KBr) Spectrum of Atorvastatin Calcium Propylene Glycol Solvate prepared from Racemic Propylene glycol DSC Thermogram obtained from the product of Example 2

IR Spectrum obtained from the product of Example 2

DSC Thermogram obtained from the product of Example 3

IR Spectrum obtained from the product of Example 3

DSC Thermogram obtained from the product of Example 4

IR spectrum obtained from the product of Example 4

DSC Thermogram obtained from the product of Example 5

IR Spectrum obtained from the product of Example 5

DSC Thermogram obtained from the product of Example 6

IR Spectrum obtained from the product of Example 6

DSC Thermogram obtained from the product of Example 8

IR Spectrum obtained from the product of Example 8

DSC Thermogram obtained from the product of Example 9

IR spectrum obtained from the product of Example 9

ATORVASTATIN CALCIUM PROPYLENE GLYCOL SOLVATES

CROSS REFERENCE TO RELATED APPLICATION

This application is a divisional application of U.S. patent application Ser. No. 11/808,942, filed Jun. 14, 2007, which claims the benefit of U.S. Provisional Application No. 60/897,106 filed Jan. 24, 2007.

FIELD OF THE INVENTION

The present invention relates to new solvated forms of atorvastatin calcium, namely propylene glycol solvates,

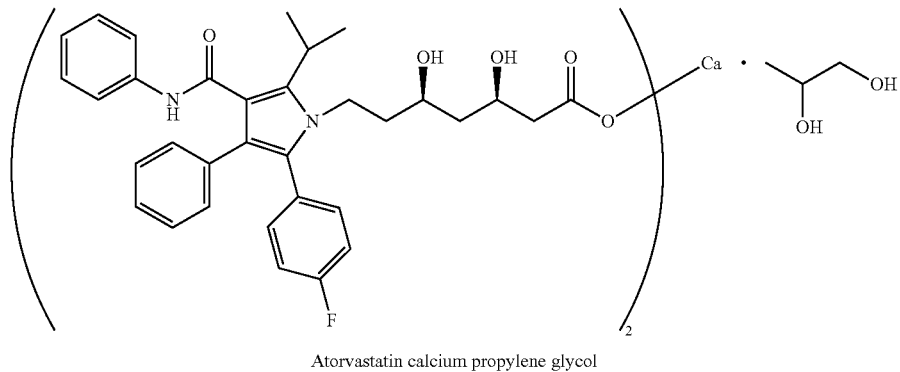

Atorvastatin calcium propylene glycol and methods for their preparation. These solvate forms are particularly well-suited for pharmaceutical applications.

BACKGROUND OF THE INVENTION

Atorvastatin is a reductase inhibitor of the enzyme 3-hydroxy-3-methylglutarate-coenzyme A (HMG-CoA) and therefore is a useful anti-hyperlipoproteinemic agent. It has proven to be a highly effective medicament for the treatment of disorders such as hyperlipidemia and hypercholesterolemia which are conditions that are known risk factors for arteriosclerosis and coronary heart disease. Atorvastatin is chemically R—(R*,R*)]-2-(4-fluorophenyl)-β,δ-dihydroxy-5-(1-methylethyl)-3-phenyl-4-(phenylcarbamoyl)-1H-pyrrole-1-heptanoic acid and is marketed as its calcium salt trihydrate under the brand name Lipitor®, wherein a 2:1 molar ratio between atorvastatin and calcium ion exists. Herein the chemical name R—(R*,R*)]-2-(4-fluorophenyl)-β,δ-dihydroxy-5-(1-methylethyl)-3-phenyl-4-(phenylcarbamoyl)-1H-pyrrole-1-heptanoic acid calcium salt is designated as atorvastatin calcium. In its dosage forms, atorvastatin calcium is currently ranked first in world-wide pharmaceutical sales.

The inhibition of the biosynthesis of cholesterol by atorvastatin was reported in U.S. Pat. No. 5,273,995. In this patent, it was indicated that the calcium salt form of the ring-opened lactone was most effective in terms of formulation.

Processes for the manufacture of atorvastatin and key synthetic intermediates have been described in various patents including U.S. Pat. Nos. 4,681,893, 5,003,080, 5,097,045, 5,103,024, 5,124,482, 5,149,837, 5,155,251, 5,216,174, 5,245,047, 5,248,793, 5,280,126, 5,397,792 and 5,342,952, U.S. Pat. No. 7,112,604 and US 2006/0199855. Typically, the final stages of the process involve the conversion of the precursor lactone [(2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide, FIG. 2 (and referred to herein as atorvastatin lactone) into atorvastatin calcium, by base hydrolysis and exchange of cation to calcium.

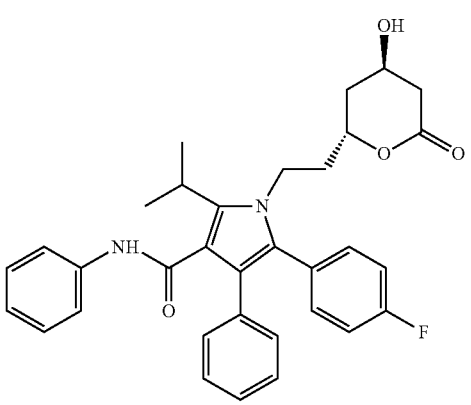

Figure 2

Since atorvastatin calcium is a chiral, non-racemic molecule and because the drug is required in high purity for pharmaceutical purposes, it is important to have efficient and effective synthetic methods to remove undesired stereoisomeric impurities. Common techniques include the formation of a chiral salt often by using an expensive chiral base. Furthermore, this approach requires extra steps (salt formation, separation, free-basing). Other methods utilize stereoselective chemical transformation. However, these often require specialized reagents and highly-controlled reaction conditions.

F. Toda in *Top. Curr. Chem. Vol.* 140, pp. 43-69, 1987 provide examples of resolving chiral compounds by the formation of inclusion complexes. This approach has, to the knowledge of the inventors, been rarely used in organic chemistry and has never, to their knowledge, been used for the industrial preparation of pharmaceutical actives. This may be due to the fact that Toda's approach requires the restrictive combination that the substrate and chiral solvating agent must form a strong solvate and one that permits an effective separation.

With respect to atorvastatin calcium, a molecule which has two chiral centres, a cost-effective and high-yielding process to remove undesired stereoisomeric impurities would be advantageous.

Many processes have been proposed to prepare various polymorphic and pseudopolymorphic forms of atorvastatin calcium which all have varying degrees of stability, aqueous solubility, ease of preparation, hygroscopicity, bioavailability, etc. In particular, one of the most significant properties to improve would be to find a form that would offer improved stability which would result in a product having longer shelf-life. Atorvastatin calcium in an amorphous state, for example, is known to suffer from reduced stability with respect to, for example, photodecomposition (Tetrahedron, Vol. 49, pp. 1979-1984, 1993).

Solvated and hydrated forms of atorvastatin calcium include an acetone solvate (WO 2006/012499) as well as ethanol and butanol solvates (US 2005/0004206). Many hydrated forms of atorvastatin calcium are known and are taught, for instance in U.S. Pat. No. 5,969,156, U.S. Pat. No. 5,298,627, U.S. Pat. No. 6,992,194 and U.S. Pat. No. 6,605,729. As previously mentioned, the currently marketed form of atorvastatin calcium is a trihydrate form.

A proposed method to stabilize atorvastatin calcium is taught in US 2005/0106243 whereby free-flowing, pulverized adsorbates of atorvastatin calcium are disclosed. Preferably, the atorvastatin calcium is in a finely dispersed, amorphous form. These adsorbates are prepared by suspending atorvastatin calcium and an adsorber material in an organic solvent containing less than 10% water followed by evaporative solvent removal.

The use of propylene glycol as a solvating agent for selected pharmaceuticals is known, for instance Celecoxib (US 2006/0052432), Olanzapine (US 2006/0223794), Eplerenone (US 2005/0267302), Azithromycin (U.S. Pat. No. 6,977,243, U.S. Pat. No. 7,105,179), Conazoles (US 2004/0019211), Cefatrizine (JP 01290682), and Cephalosporin compounds (U.S. Pat. No. 4,091,213, U.S. Pat. No. 3,970,651, JP 105,813/75 and CA 1,101,840). A general patent application WO 2004/060347, which is related to the above Celecoxib and Olanzapine patent applications, suggests the general possibility of propylene glycol solvated forms of active pharmaceuticals and provides a lengthy list (>3000) including atorvastatin. However, details are only provided for only selected examples.

Given the difficulties associated with finding suitable processes to produce pharmaceutically pure and oxidatively stable forms of atorvastatin calcium, new and industrially acceptable solutions, which offer advantages relative to the prior art, were required.

It is therefore an object of this invention to provide new solvated forms of atorvastatin calcium and processes for their preparation.

Further and other objects of the invention will be realized by those skilled in the art from the following Summary of the Invention and Detailed Description of Preferred Embodiments of the Invention thereof.

SUMMARY OF THE INVENTION

We surprisingly have discovered the common diol food additive, propylene glycol (1,2-propanediol), which can exist as either one of two enantiomers or as their mixture, forms crystalline solvates with atorvastatin calcium in a 1:1 molar ratio. Further, these atorvastatin calcium propylene glycol solvates show remarkable stability, can be easily purified, and thereafter may be formulated into effective dosage forms.

The use of propylene glycol as a solvating agent has many advantages. It is inexpensive and widely-available, having many industrial applications including use as a moisturizer for medicines, cosmetics, food and tobacco products and as a humectant food additive. Furthermore, it has an established safety profile and can be purchased as pharmaceutically acceptable USP NF-grade material. For instance, it is listed as a Food Additive in FDA's "*Everything" Added to Food in the United States* (EAFUS)" database (http://www.cfsan.fda.gov/~dms/eafus.html).

The atorvastatin calcium propylene glycol solvates of this invention are crystalline and are efficiently prepared from various forms of atorvastatin calcium and either (R), (S), or mixtures of (R) and (S) propylene glycol. Atorvastatin calcium propylene glycol solvates of the present invention have many desirable characteristics, including low hygroscopicity, good flow properties, and high chemical and solid state stability. Also, the atorvastatin calcium propylene glycol solvates of the present invention may be easily filtered and dried, even on an industrial scale. By formation of this solvate, it also serves to further purify the atorvastatin calcium.

Propylene glycol can be obtained in either enantioenriched (R) or (S) forms, or as an equal or unequal mixture of enantiomers. The racemic mixture (wherein equal amounts of the (R) and (S) enantiomers are present) of propylene glycol has better availability and is less expensive. However, we have discovered that racemic propylene glycol, as well as substantially (R) or (S) propylene glycol, can be utilized to improve the optical purity of atorvastatin calcium due to a preferential formation of a solvate containing one of the enantiomeric forms of propylene glycol. This result is demonstrated by Example 7 where atorvastatin propylene glycol solvate, prepared from racemic propylene glycol [i.e., a 1:1 mixture of (R) and (S)-propylene glycol], was desolvated to provide propylene glycol which was enriched in the (R)-enantiomer. This represents a highly desirable and effective method to improve the stereochemical purity of atorvastatin calcium and addresses the requirement for the high stereochemical purity in pharmaceutical products. This process can be repeated to further enhance either the stereochemical and/or chemical purity of atorvastatin. Resolutions of this type are exceedingly rare in organic chemistry and are the unexpected and surprising result of our research.

An object of the present invention is Atorvastatin calcium propylene glycol solvates. Preferably, an atorvastatin calcium propylene glycol solvate where the molar ratio of atorvastatin calcium to propylene glycol is about 1:1. Also preferably, the atorvastatin calcium propylene glycol solvate where the propylene glycol component has predominantly the (R) absolute configuration. Also preferably, the atorvastatin calcium propylene glycol solvate where the propylene glycol component has predominantly the (S) absolute configuration. Also preferably, the atorvastatin calcium propylene glycol solvate of claim 1, wherein said propylene glycol is present in any proportion of the (R) and (S) absolute configuration provided the proportion of the (R) and (S) propylene glycol is not about 1:1.

Another object of the present invention is to provide an Atorvastatin calcium propylene glycol solvate when prepared in a manner comprising the steps of:
(a) adding atorvastatin calcium to propylene glycol;
(b) adding an organic co-solvent;
(c) optionally adding water, and
(d) isolating and optionally drying the isolated solvate by filtration.

Yet another object of the present invention is to provide a process for preparing atorvastatin calcium propylene glycol solvate comprising the steps of:
(a) adding atorvastatin calcium to propylene glycol;
(b) adding an organic co-solvent;
(c) optionally adding water, and
(d) isolating and optionally drying the isolated solvate by filtration.

Preferably, the organic co-solvent is selected from the group consisting of C3 to C5 alkyl esters and C3 to C6 alkyl ketones, and mixtures thereof. More preferably the organic co-solvent comprises ethyl acetate and isopropyl acetate. Most preferably the organic co-solvent comprises methyl isobutyl ketone. Preferably, step (c) is carried out using from about 0 to about 2 volumes of water.

Also preferably, step (b) is carried out using from about 5 to about 9 volumes of organic co-solvent. Also preferably, step (a) is carried out using from about 5 to about 9 volumes of organic co-solvent. Preferably, step (a) is carried out using from about 0.5 to about 4 volumes of propylene glycol. Preferably, step (a) is carried out using R-propylene glycol or S-propylene glycol.

Another object of the present invention is to provide a process for the purification of atorvastatin calcium by formation of propylene glycol solvates of atorvastatin calcium and thereafter desolvation of the atorvastatin calcium propylene glycol solvates and recovery of atorvastatin calcium.

Another object of the present invention is to provide a process for the preparation of atorvastatin calcium and propylene glycol by using the solvates of the present invention and desolvating them to produce atorvastatin calcium and propylene glycol.

DESCRIPTION OF PREFERRED
EMBODIMENTS OF THE INVENTION

Atorvastatin calcium propylene glycol solvates may be prepared in various ways. For instance, atorvastatin calcium may be added to propylene glycol and an organic solvent, optionally in the presence or absence of water, and the mixture stirred and optionally heated. The mixture may be either homogenous or heterogeneous at this stage. Preferred organic solvents include C3 to C5 alkyl esters, most preferably ethyl acetate and isopropyl acetate and C3 to C6 alkyl ketones, most preferably methyl isobutyl ketone, and mixtures thereof. The amounts, relative to atorvastatin calcium, of propylene glycol, organic co-solvent and water are about from 0.5 to about 4 volumes, from about 5 to about 9 volumes, and about 0 to about 2 volumes, respectively. The solution is cooled from between about −5° C. to about 30° C., more preferably from between about 0° C. to about 25° C., most preferably from between about 0° C. to about 5° C. The obtained propylene glycol solvates are generally isolated by filtration and, in order to remove the mother liquor, can be optionally rinsed with an organic solvent selected from a C3 to C5 alkyl esters, most preferably ethyl acetate or a C3 to C6 alkyl ketones, most preferably methyl isobutyl ketone or acetone, or a C4 to C8 cyclic or acyclic alkyl ethers, most preferably methyl tert-butyl ether (MTBE). The isolated atorvastatin calcium propylene glycol solvates may be dried further in, for instance, a vacuum oven at about 20 mmHg vacuum or less and from about 30° C. to about 90° C., more preferably from about 50° C. to about 60° C.

A variation of the above method with respect to the isolation of the atorvastatin propylene glycol solvate is to evaporate the solvent, after solvate formation, and add an organic solvent. Preferred solvents include C3 to C5 alkyl esters, most preferably ethyl acetate and isopropyl acetate and C3 to C6 alkyl ketones, most preferably methyl isobutyl ketone, and mixtures thereof. The amount of organic co-solvent used in this isolation procedure would be from about 5 to about 9 volumes. The mixture is heated and stirred and the precipitated solid is isolated by filtration and dried.

In another embodiment of the invention, atorvastatin calcium propylene glycol solvates may be prepared optionally from atorvastatin calcium of any polymorphic or pseudopolymorphic form or directly from other atorvastatin precursors such as, for example, atorvastatin lactone, atorvastatin N-methylglucamine salt or (4R-cis)-1,1-dimethylethyl-6-{2-[[2-

(4-fluorophenyl)]-5-(1-methylethyl)-3-phenyl-4-[(phenylamino)carbonyl]-1H-pyrrole-1-yl]ethyl}-2,2-dimethyl-1,3-dioxane-4-acetate.

In another embodiment of the invention, atorvastatin calcium propylene glycol solvates may be desolvated to separate atorvastatin calcium from propylene glycol.

Figure 1:
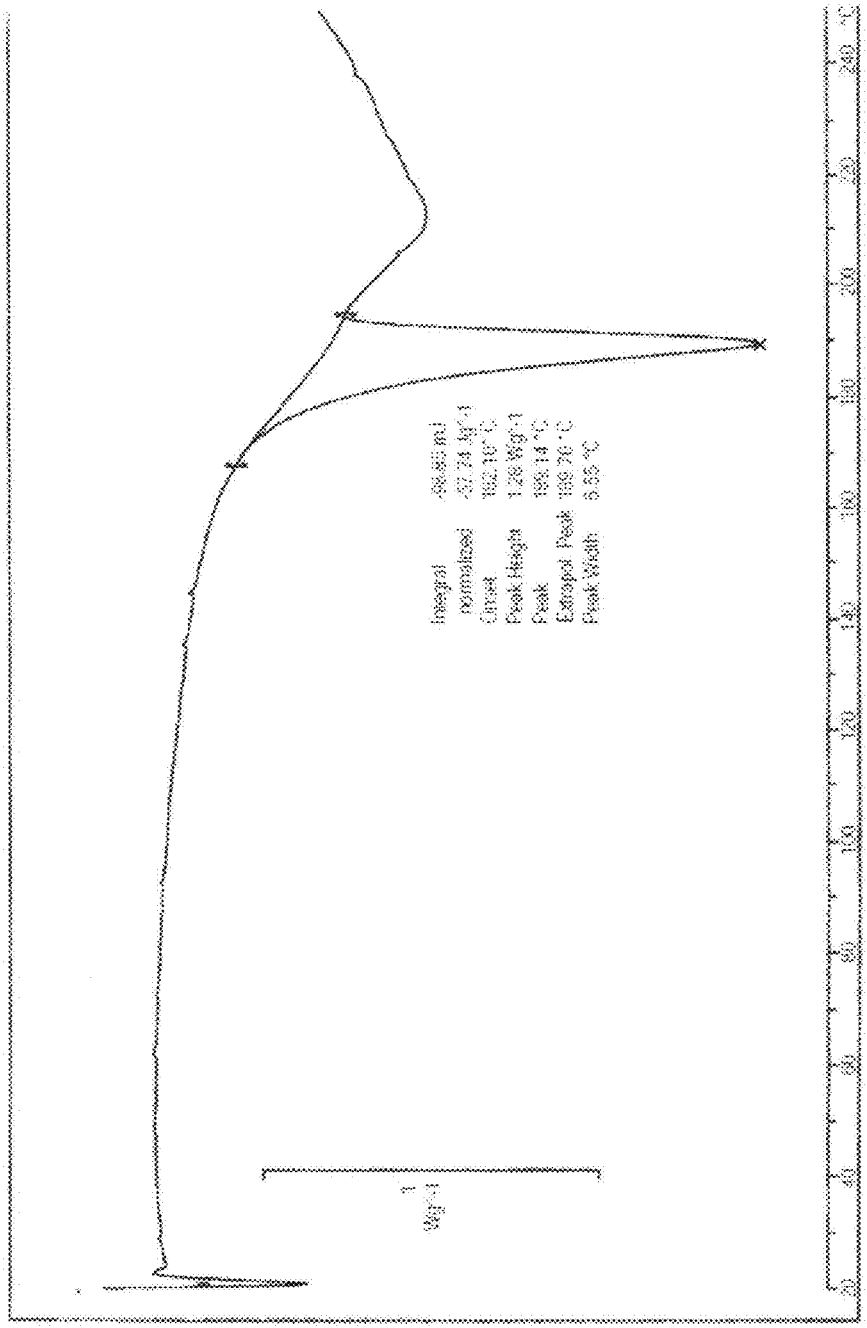
FIG. 1 shows a DSC Thermogram of Atorvastatin Calcium Propylene Glycol Solvate prepared from racemic propylene glycol according to Example 1.

Atorvastatin calcium propylene glycol solvates prepared by the process of the present invention can be characterized by a Differential Scanning calorimetry (DSC) Thermogram exhibiting a major endotherm at a peak onset temperature of about 183° C. and a peak maximum of about 192° C. The crystalline atorvastatin calcium propylene glycol solvate prepared by the process of the present invention can be further characterized by a DSC thermogram as shown in FIG. 1.

Atorvastatin calcium propylene glycol solvates prepared the process of the present invention can be characterized by their IR spectra (1% KBr) exhibiting characteristic adsorption at about 3382, 1652, 1510, 1436, 1315, 1221, and 844 cm$^{-1}$.

Atorvastatin calcium propylene glycol solvates prepared by the process of the present invention can be further characterized by IR spectrometry. A representative IR spectrum (taken in 1% KBr) is shown as FIG. 2.

The following examples are merely representative of the present invention and are not intended to be limiting.

EXAMPLE 1

Preparation of Atorvastatin Calcium Propylene Glycol Solvate Under Anhydrous Conditions Atorvastatin calcium (5 g) was dissolved in racemic propylene glycol followed by the addition of 7 parts of ethyl acetate. The resulting mixture was warmed to 55-60° C. and stirred for 8-10 hours to afford a white suspension. The suspension was cooled to 20-25° C. and filtered to provide 3.3 g of atorvastatin calcium propylene glycol solvate after drying under vacuum at 50-60° C. Propylene glycol content: 6% by NMR.

Isopropyl acetate and methyl, isobutyl ketone (MIBK) can also be used in the example 1 procedure.

Figure 2:
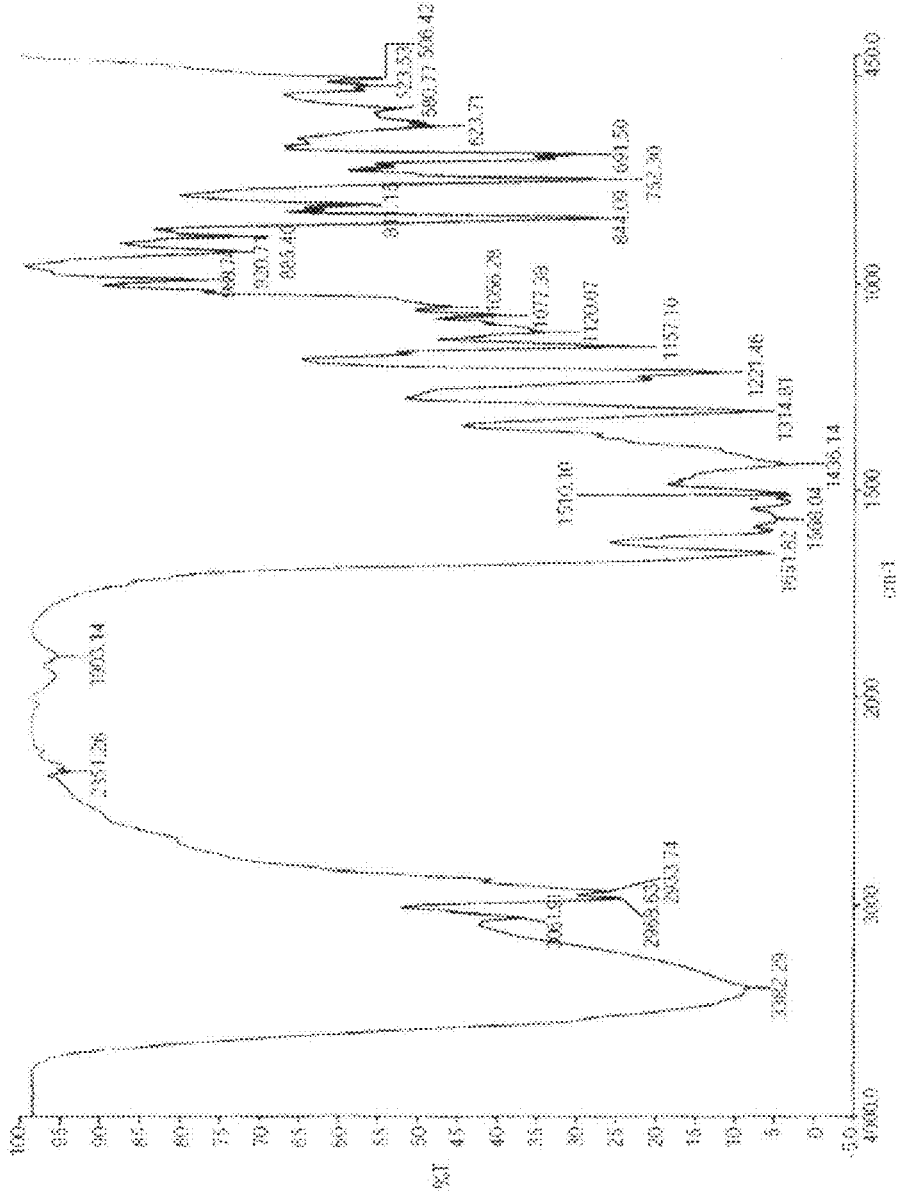
FIG. 2 shows an IR (KBr) Spectrum of Atorvastatin Calcium Propylene Glycol Solvate prepared from racemic propylene glycol according to Example 1.

The DSC and IR of the solvate made in this example is shown in FIGS. 1 and 2, respectively.

$^1$H-NMR (DMSO-d$_6$): δ 9.82 (s, 1H), 7.51 (ad, J=8.0 Hz, 2H), 7.33-7.11 (m, 6H), 7.08-6.95 (m, 6H), 5.93 (bs, 1H), 4.76 (bs, 1H), 4.65-4.33 (m, 1H), 4.09-3.85 (m, 1H), 3.84-3.68 (m, 2H), 3.62-3.44 (m, 1.5H), 3.30-3.09 (m, 2H), 2.08 (dd, J=15.4, 3.7 Hz), 1.97 (dd, J=15.3, 8.0 Hz), 1.71-1.50 (m, 2H), 1.50-1.31 (m, 7H), 1.30-1.11 (m, 1H), 1.00 (d, J=6.3 Hz, 1.5H).

EXAMPLE 2

Figure 3:
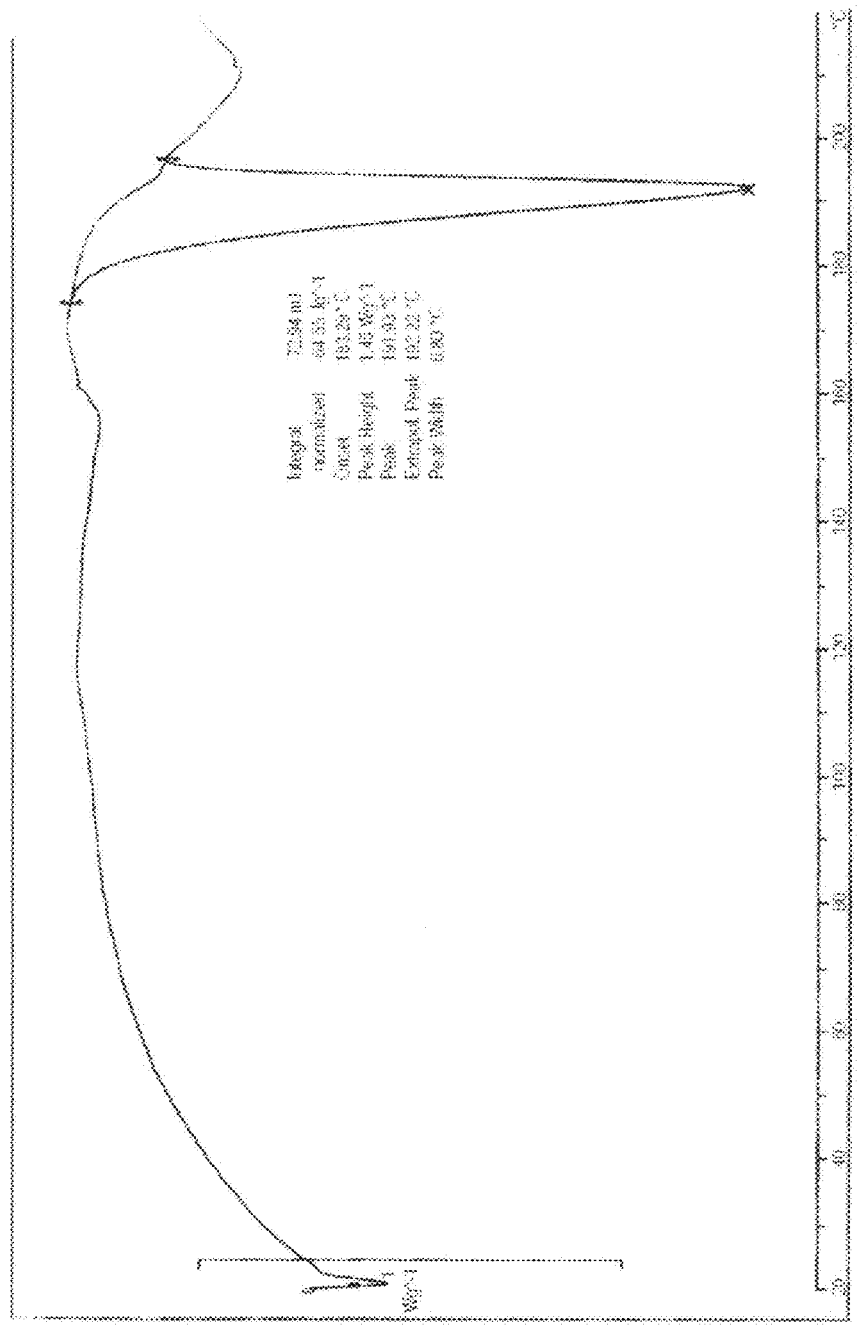
FIG. 3 shows a DSC Thermogram obtained from the product of Example 2.
Figure 4:
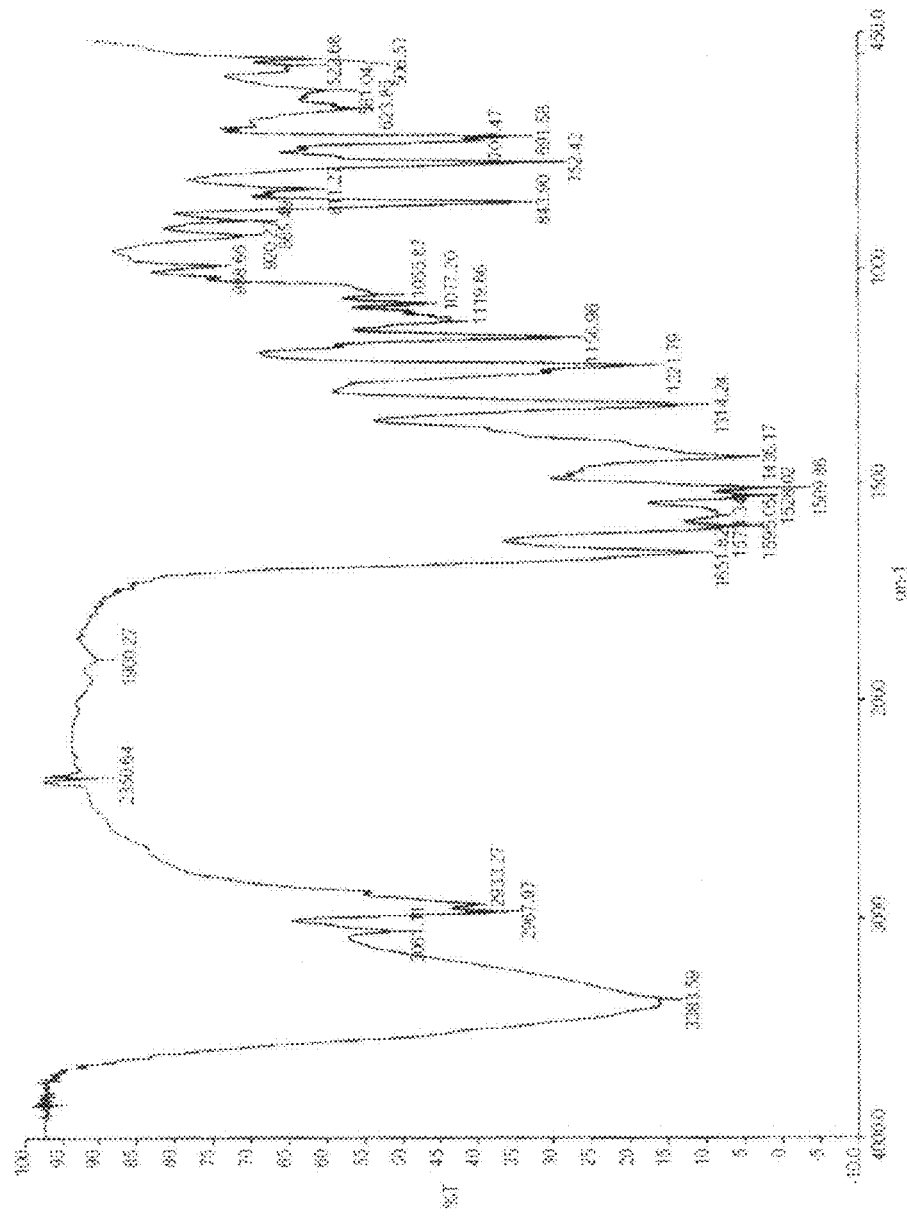
FIG. 4 shows an IR spectrum obtained from the product of Example 2.

Preparation of Atorvastatin Calcium Propylene Glycol Solvate Under Hydrous Conditions Atorvastatin calcium (10 g) was dissolved in racemic propylene glycol followed by the addition of 7 parts of ethyl acetate and 0.3 parts of water. The resulting mixture was warmed to 55-60° C. and stirred for 8-10 hours to afford a white suspension. The suspension was cooled to 20-25° C. and filtered to furnish 7.4 g atorvastatin calcium propylene glycol solvate after drying under vacuum at 50-60° C. Propylene glycol content: 6% by NMR, KF=0.2%. The DSC and IR of this material are shown as FIGS. 3 and 4 respectively.

EXAMPLE 3

Figure 5:
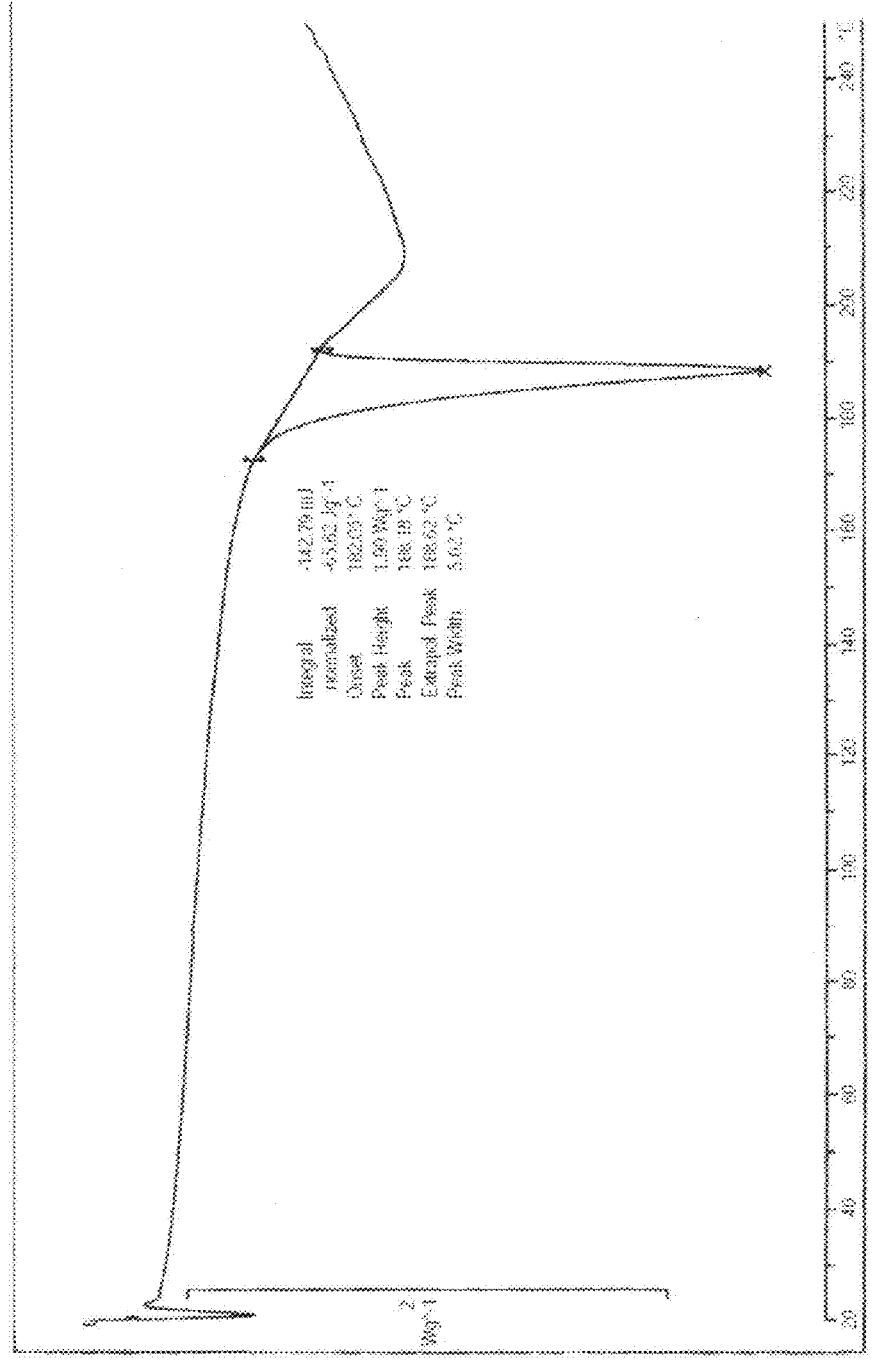
FIG. 5 shows a DSC Thermogram obtained from the product of Example 3.
Figure 6:
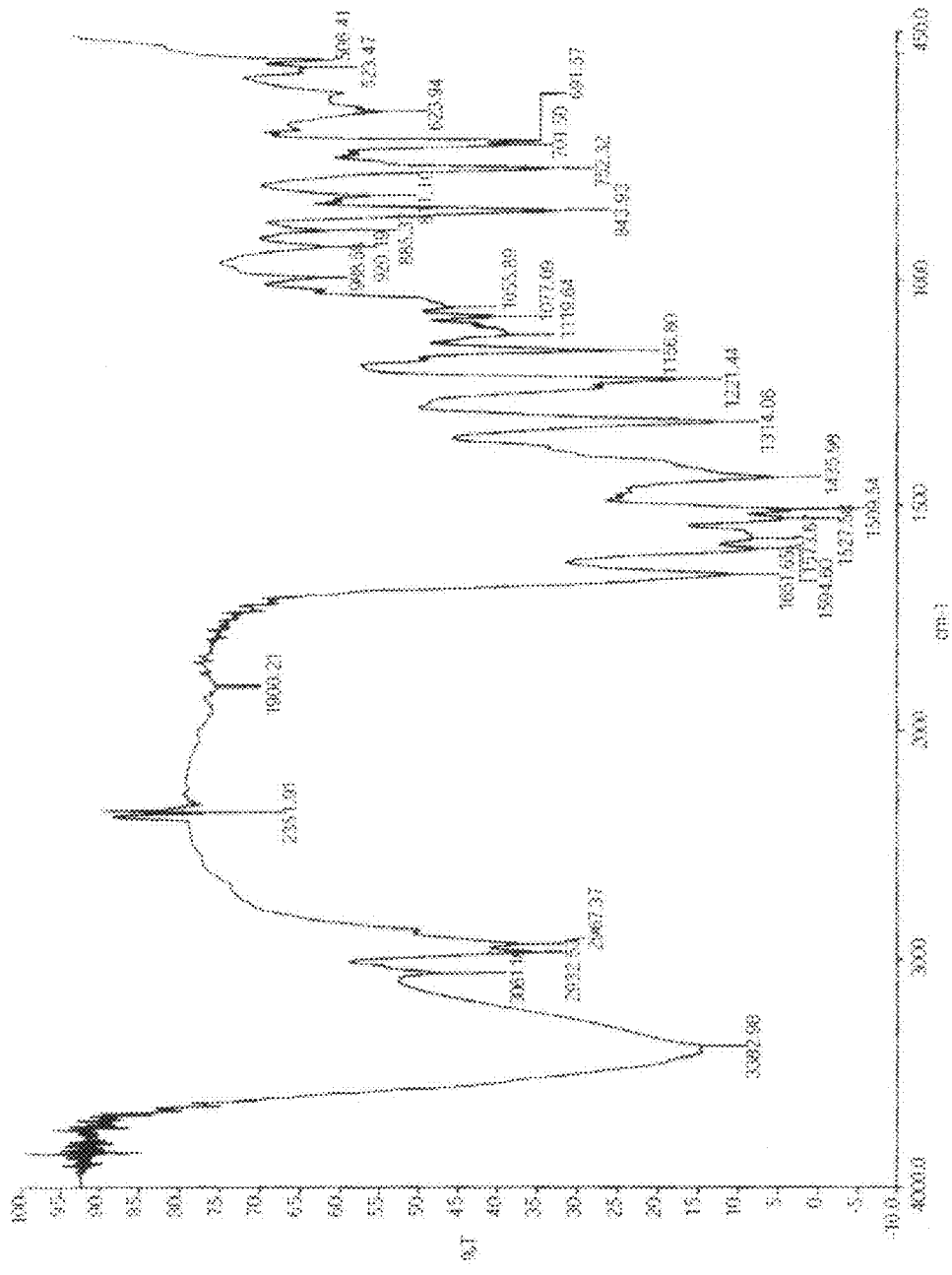
FIG. 6 shows an IR spectrum obtained from the product of Example 3.

Preparation of Atorvastatin Calcium Propylene Glycol Solvate Under Hydrous Conditions Atorvastatin calcium (5 g) was dissolved in racemic propylene glycol followed by the addition of 7 parts of MIBK and 0.6 parts of water. The resulting mixture was warmed to 55-60° C. and stirred for 8-10 hours to afford a white suspension. The suspension was cooled to 20-25° C. and filtered to give 3.8 g of atorvastatin calcium propylene glycol solvate after drying under vacuum at 50-60° C. Propylene glycol content: 6% by NMR, KF=0.2%. The DSC and IR of this material are shown as FIGS. 5 and 6 respectively.

EXAMPLE 4

Figure 7:
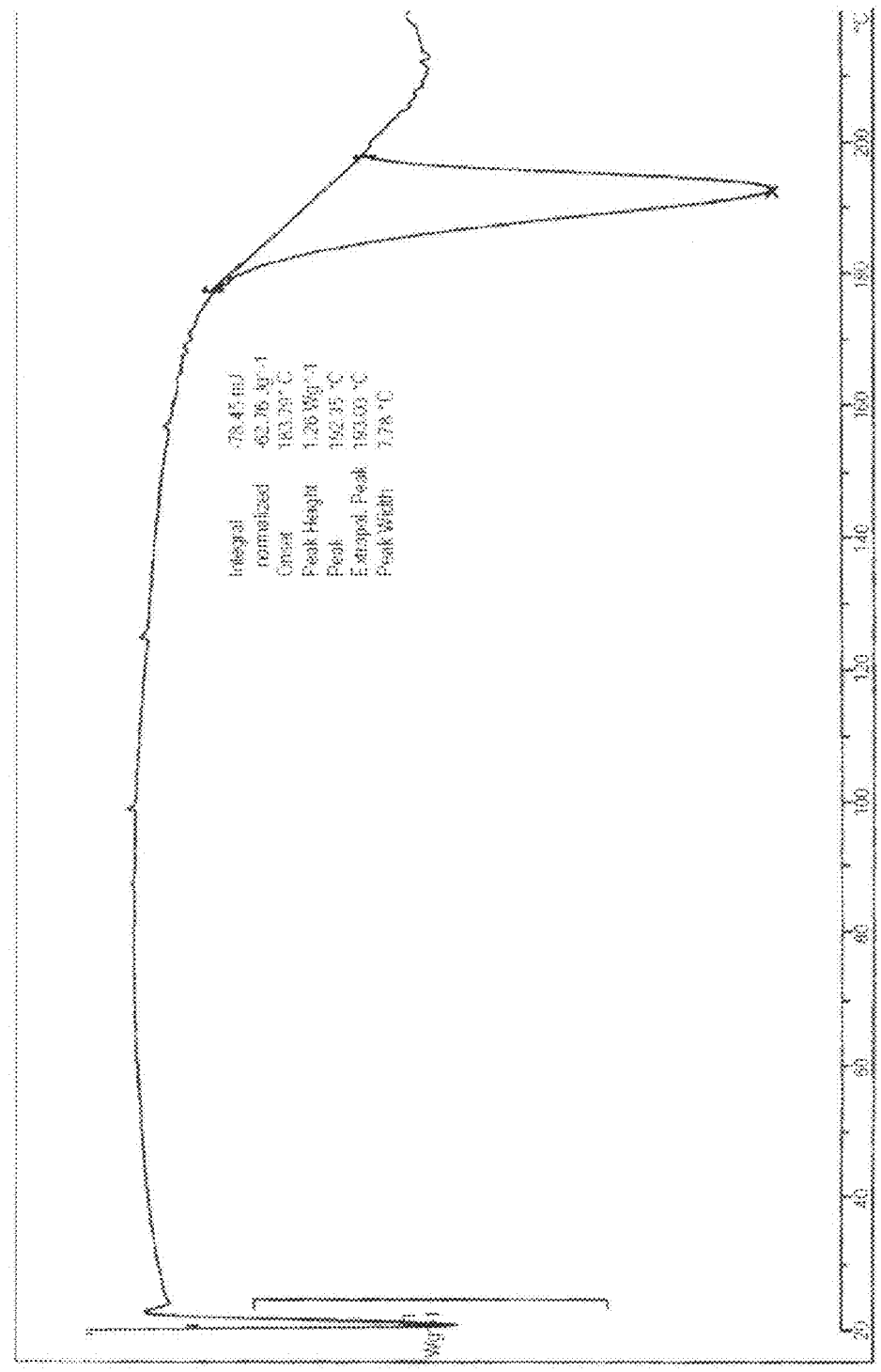
FIG. 7 shows a DSC Thermogram obtained from the product of Example 4.
Figure 8:
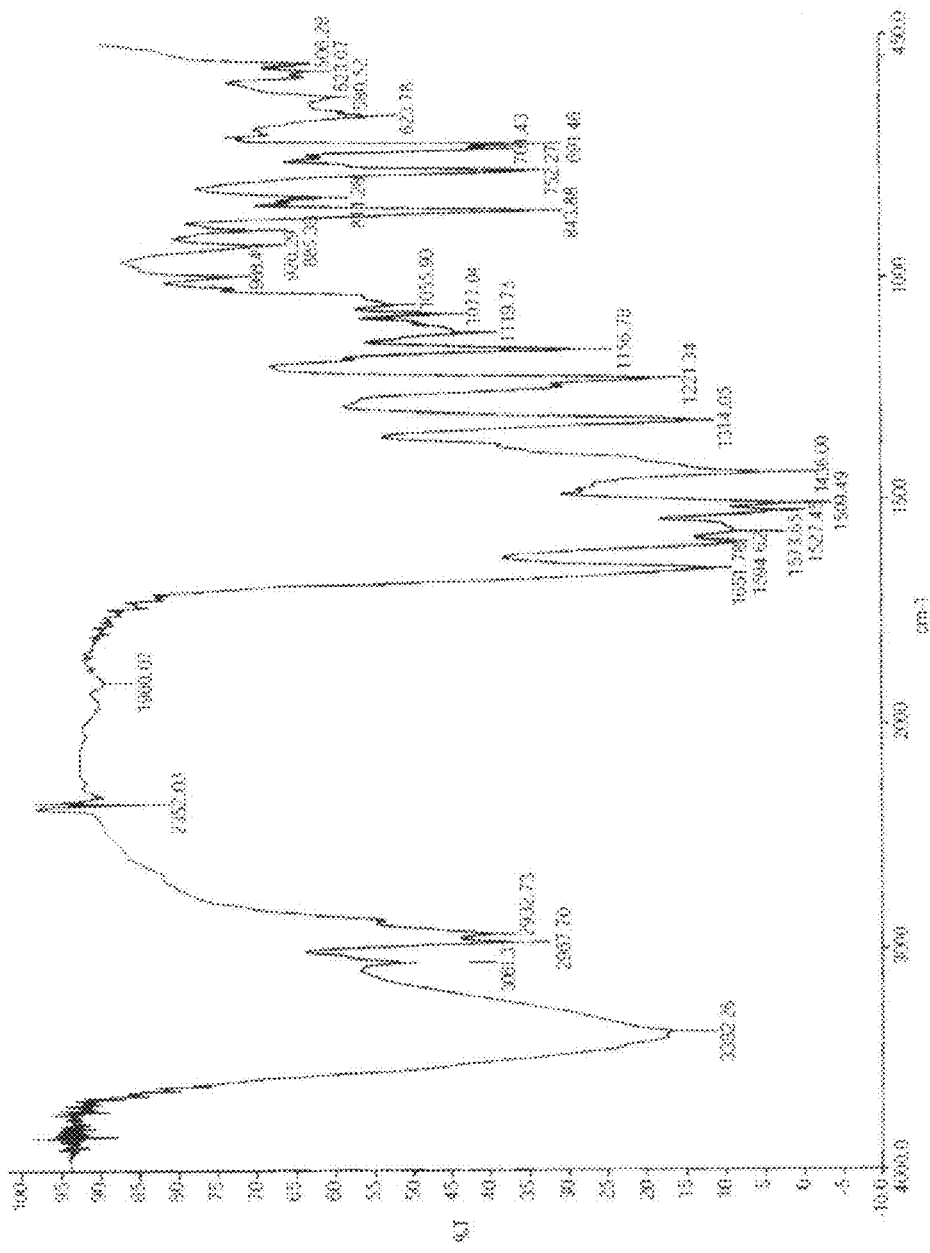
FIG. 8 shows an IR spectrum obtained from the product of Example 4.

Preparation of Atorvastatin Calcium Propylene Glycol Solvate Under Hydrous Conditions Atorvastatin calcium (130 g) was dissolved in racemic propylene glycol followed by the addition of 7 parts of isopropyl acetate and 0.6 parts of water. The resulting mixture was warmed to 55-60° C. and stirred for 8-10 hours to afford a white suspension. The suspension was cooled to 20-25° C. and filtered and the filter-cake was rinsed with 2 parts of isopropyl acetate to provide 110 g of atorvastatin calcium propylene glycol solvate after drying in a vacuum oven at 50-60° C. Propylene glycol content: 6% by NMR, KF=0.2%. The DSC and IR of this material are shown as FIGS. 7 and 8 respectively.

EXAMPLE 5

Figure 9:
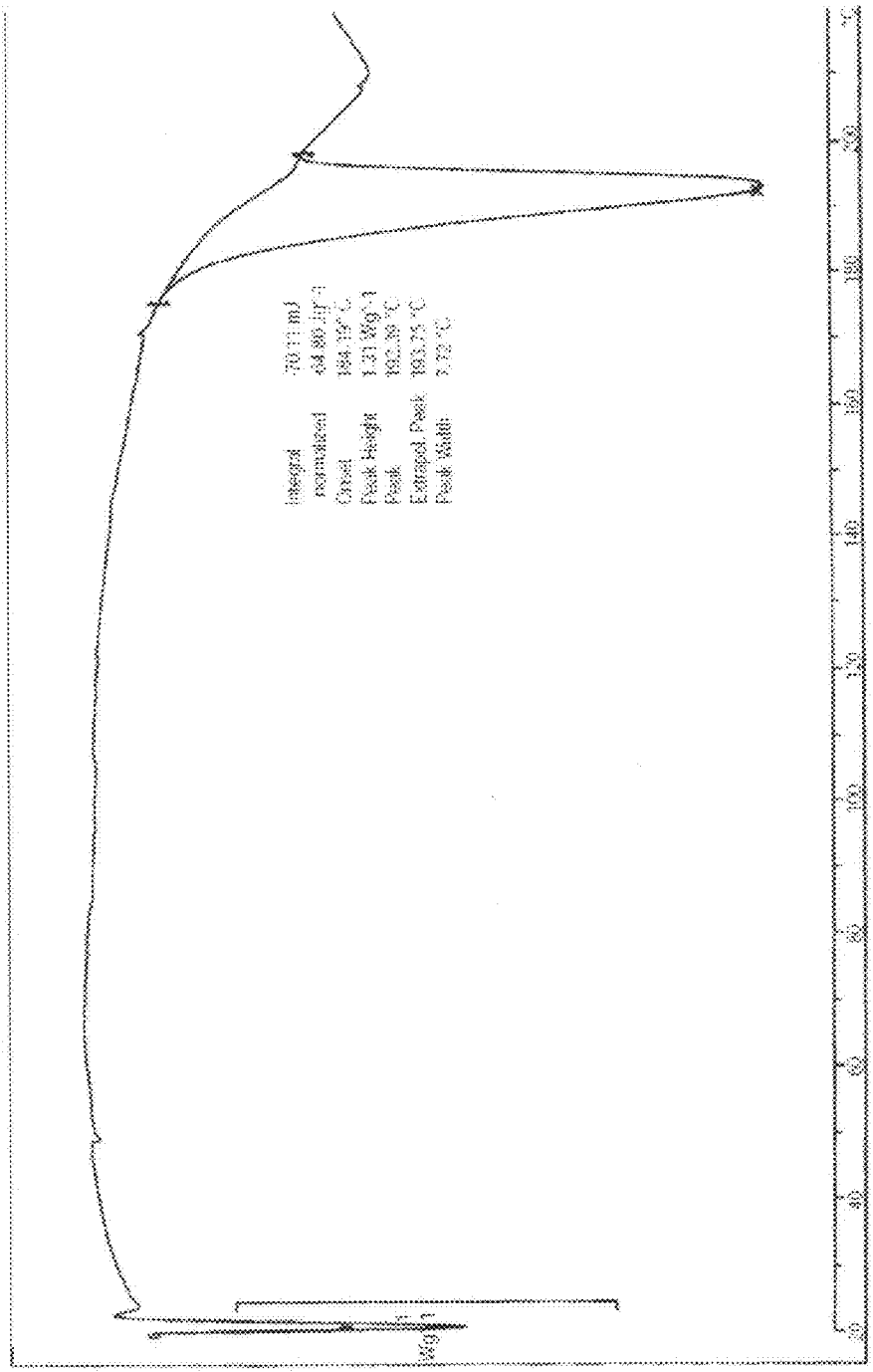
FIG. 9 shows a DSC Thermogram obtained from the product of Example 5.
Figure 10:
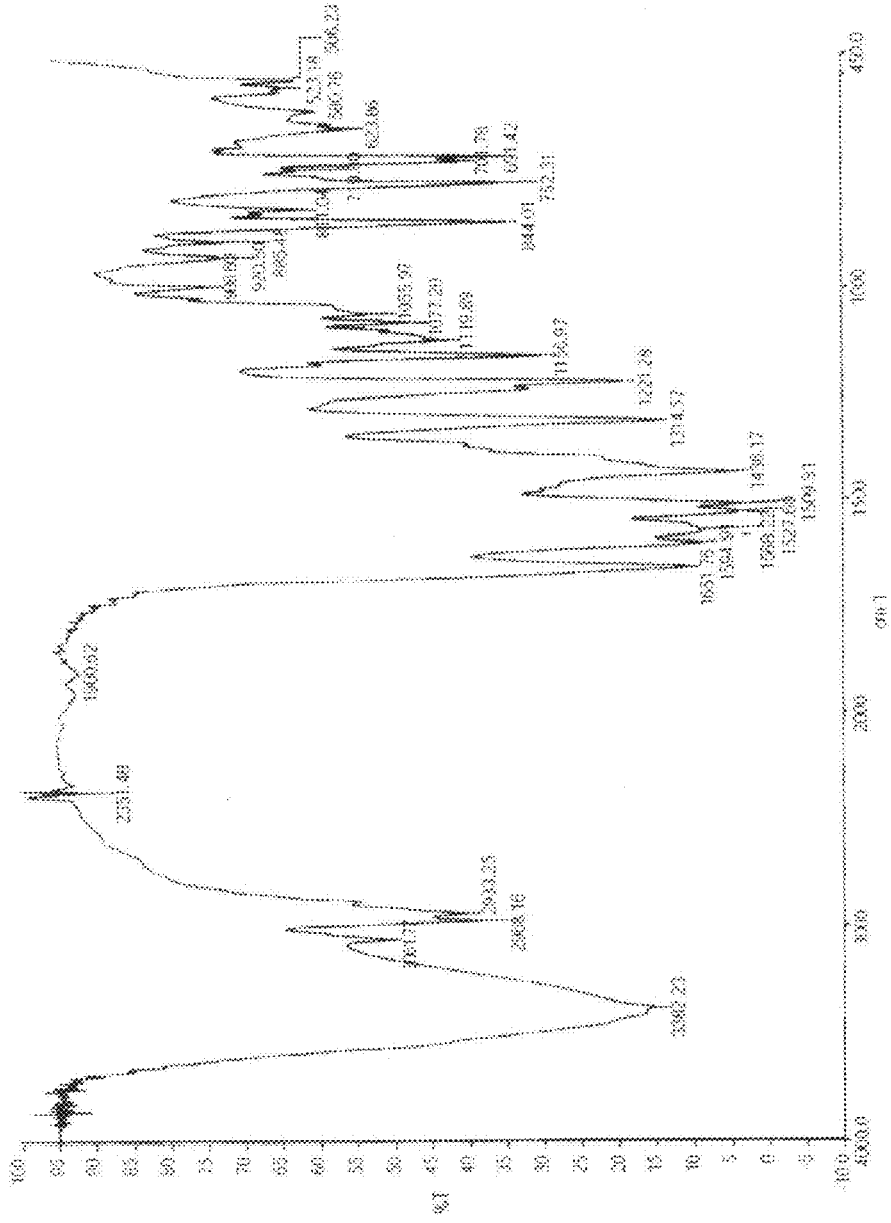
FIG. 10 shows an IR spectrum obtained from the product of Example 5.

Preparation of Atorvastatin Calcium Propylene Glycol Solvate Under Hydrous Conditions from Atorvastatin tert-butyl ester To a mixture of (4R-cis)-1,1-dimethylethyl-6-{2-[[2-(4-fluorophenyl)]-5-(1-methylethyl)-3-phenyl-4-[(phenylamino)carbonyl]-1H-pyrrole-1-yl]ethyl}-2,2-dimethyl-1,3-dioxane-4-acetate (100 g) and 10 parts MeOH was added 1 eq. 1N aq. HCl solution. The mixture was warmed to about 50° C. and maintained for about 10 h before it was cooled to room temperature. At this point, 2 eq. of 1 N NaOH solution was added and the mixture was warmed to about 60° C. for about 10 h. After cooling to room temperature the reaction mixture was acidified with diluted aqueous HCl solution and extracted three times with 2 parts of isopropyl acetate and the combined organic layers were washed with brine. To the organic solution was added 3 parts of racemic propylene glycol and 0.5 eq Ca(OH)$_2$ in 0.3 parts of water. The resulting mixture was warmed to 55-60° C. and stirred for 8-10 hours to afford a white suspension. The suspension was cooled to 20-25° C. and filtered to furnish atorvastatin calcium propylene glycol solvate after drying under vacuum at 50-60° C. Yield: 77% from the atorvastatin tert-butyl ester. Propylene glycol content: 6% by NMR, KF=0.1%. The DSC and IR of this material are shown as FIGS. 9 and 10 respectively.

EXAMPLE 6

Figure 11:
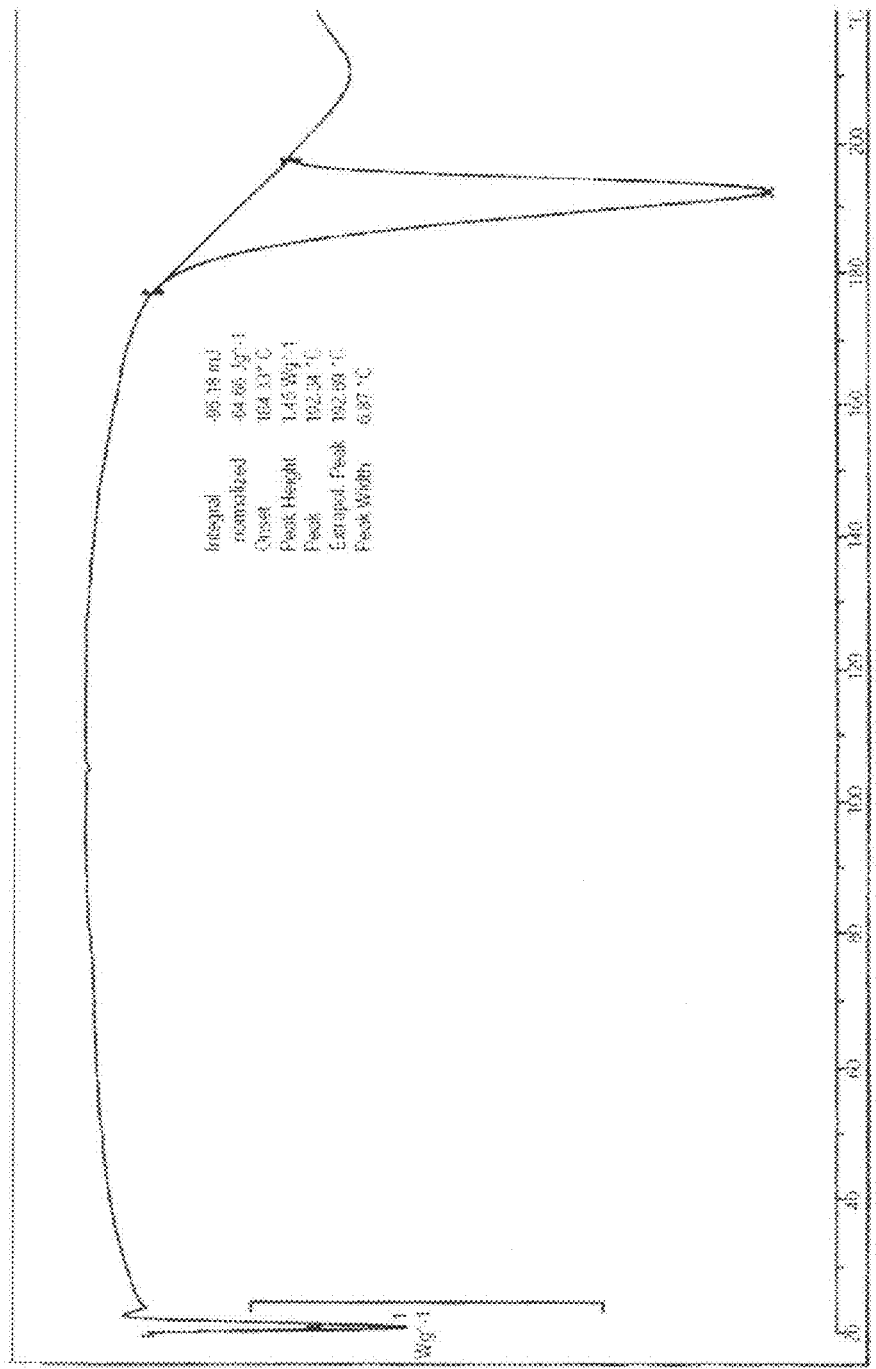
FIG. 11 shows a DSC Thermogram obtained from the product of Example 6.
Figure 12:
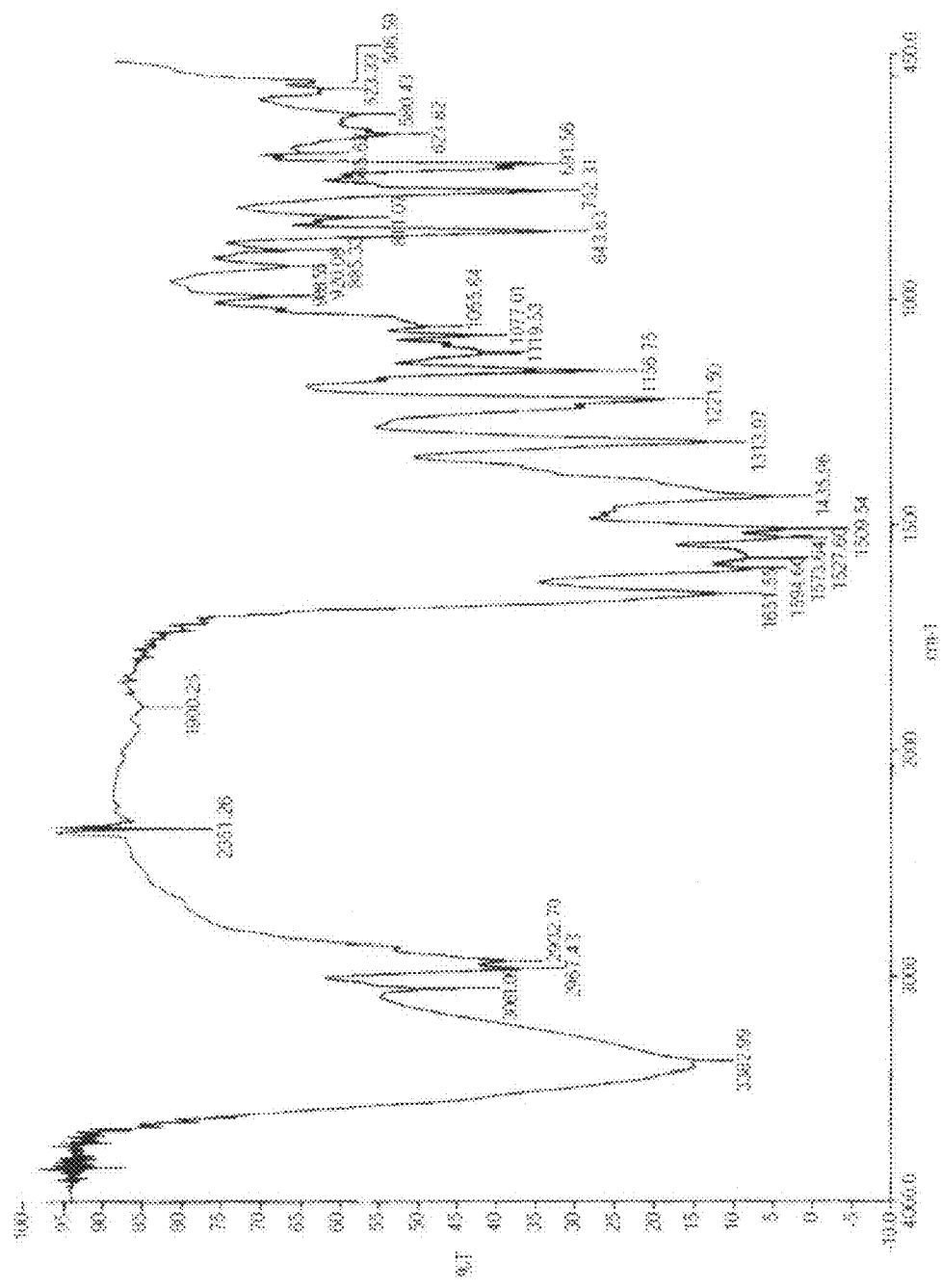
FIG. 12 shows an IR spectrum obtained from the product of Example 6.

Preparation of Atorvastatin Calcium Propylene Glycol Solvate Under Hydrous Conditions from Atorvastatin N-methylglucamine Atorvastatin N-methylglucamine (NMG) (15 g) salt was dissolved in 6 parts isopropyl acetate and 4 parts of water at room temperature. The mixture was acidified with dilute aqueous HCl solution to a pH of ~2. The organic layer was washed with brine. To the organic solution was added 3 parts of racemic propylene glycol and 0.5 eq Ca(OH)$_2$. The resulting mixture was warmed to 55-60° C. and stirred for 8-10 hours to afford a white suspension. The suspension was cooled to 20-25° C. and filtered to give atorvastatin calcium propylene glycol solvate after drying under vacuum at 50-60° C. Yield: 70% from atorvastatin tert-butyl ester; Propylene glycol content: 6% by NMR; KF=0.1%. The DSC and IR of this material are shown as FIGS. 11 and 12 respectively.

EXAMPLE 7

Desolvation of Atorvastatin Calcium Propylene Glycol Solvate

Atorvastatin calcium propylene glycol solvate was desolvated by distillation using Kugelrohr distillation. Thus, a Kugelrohr distillation flask (500 mL) was charged with 30 g of atorvastatin calcium propylene glycol solvate (as prepared according to the processes described in examples 1 to 6) was distilled at 130-140° C. under vacuum (1~1.5 mmHg). The propylene glycol was collected in the chilled receiver to afford 1.1 g propylene glycol (purity 100% by NMR). The resulting specific rotation of the propylene glycol was −8.36° (c=7.5 in water) indicating that it is enriched in the R-enantiomer and confirming the preferential formation of atorvastatin R-propylene glycol solvate.

EXAMPLE 8

Preparation of Atorvastatin Calcium (R)-propylene Glycol Solvate

Figure 13:
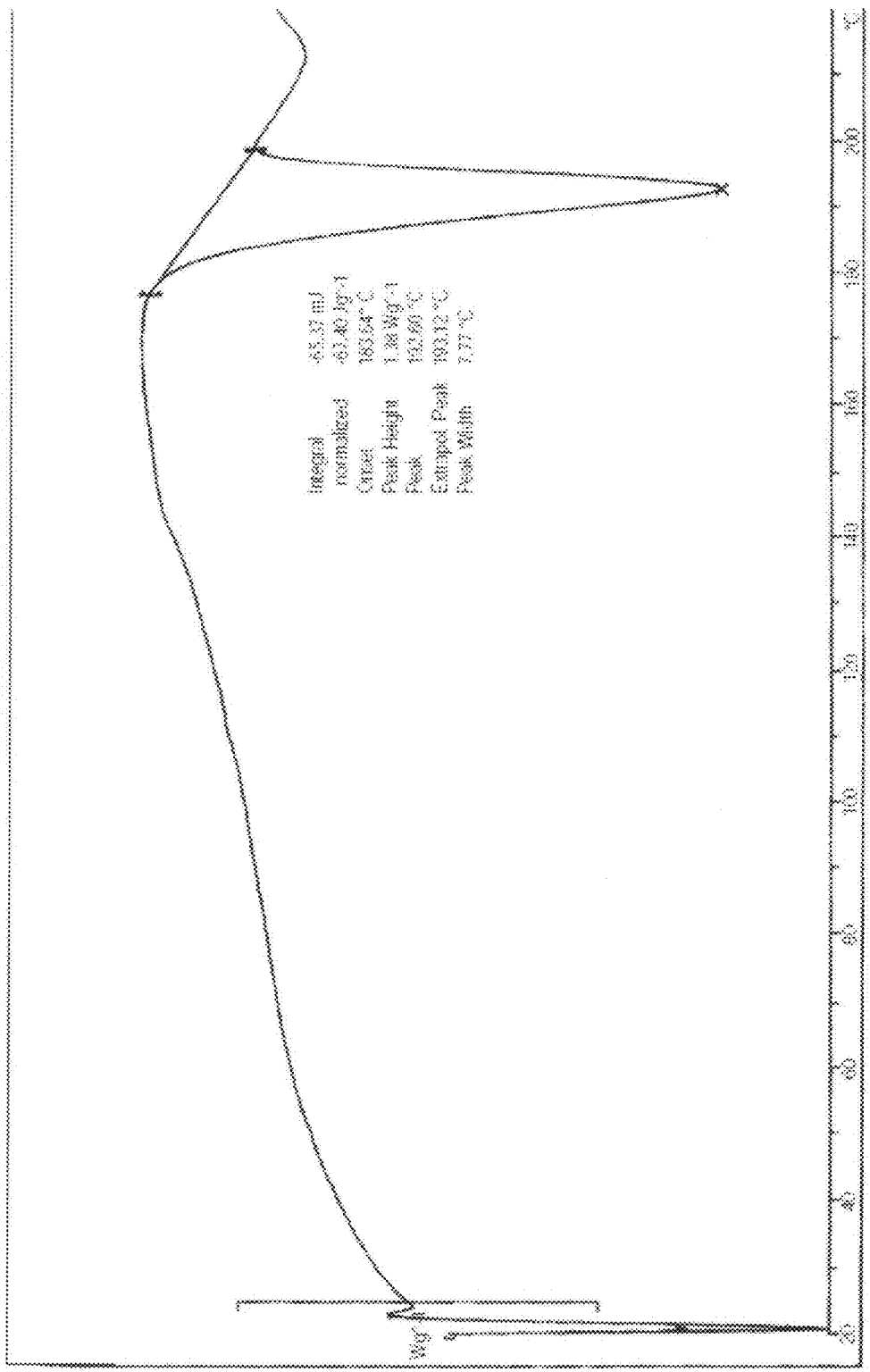
FIG. 13 shows a DSC Thermogram obtained from the product of Example 8.
Figure 14:
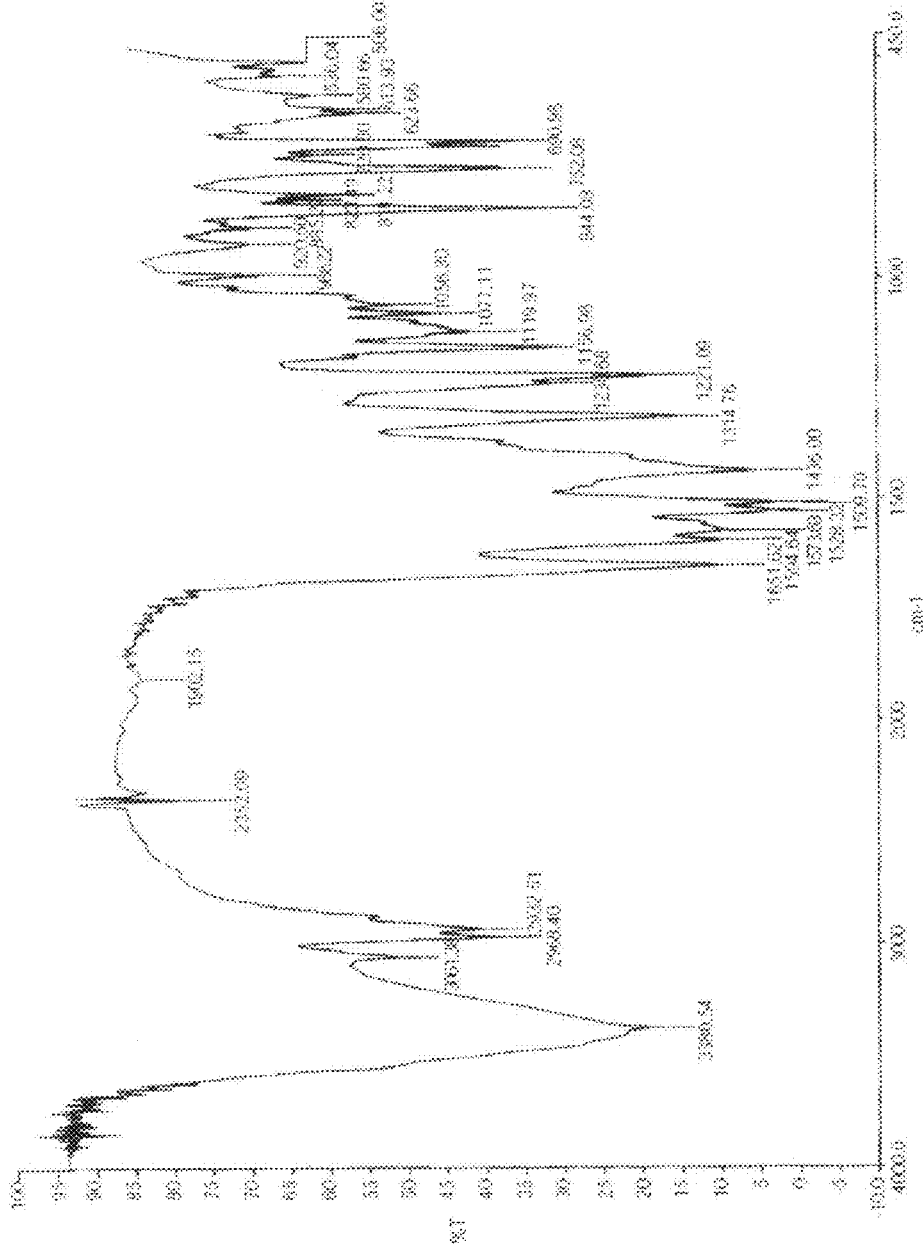
FIG. 14 shows an IR spectrum obtained from the product of Example 8.

Atorvastatin calcium (1 g) was dissolved in 2 mL of (R)-propylene glycol followed by the addition of 7 mL of isopropyl acetate and 0.6 mL of water. The resulting mixture was warmed to 55-60° C. and stirred for 8-10 hours to afford a white suspension. The suspension was cooled to 20-25° C. and filtered and dried under vacuum at 50-60° C. to give 0.7 g Atorvastatin calcium (R)-propylene glycol solvate. (R)-Propylene glycol content: 6.3% by NMR, KF=0.2%. The DSC and IR of this material are shown as FIGS. 13 and 14 respectively.

EXAMPLE 9

Preparation of Atorvastatin Calcium (S)-propylene Glycol Solvate

Figure 15:
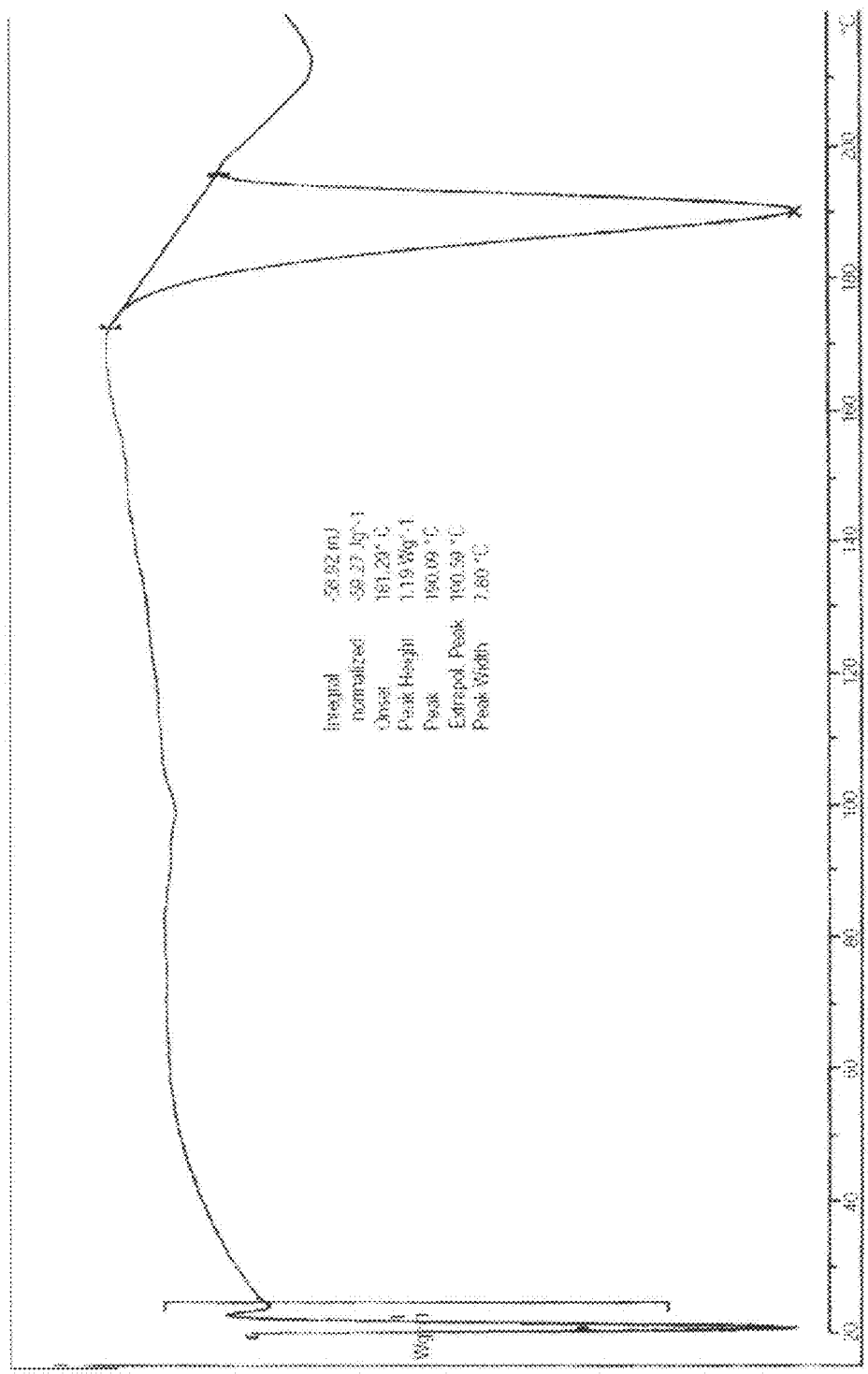
FIG. 15 shows a DSC Thermogram obtained from the product of Example 9.
Figure 16:
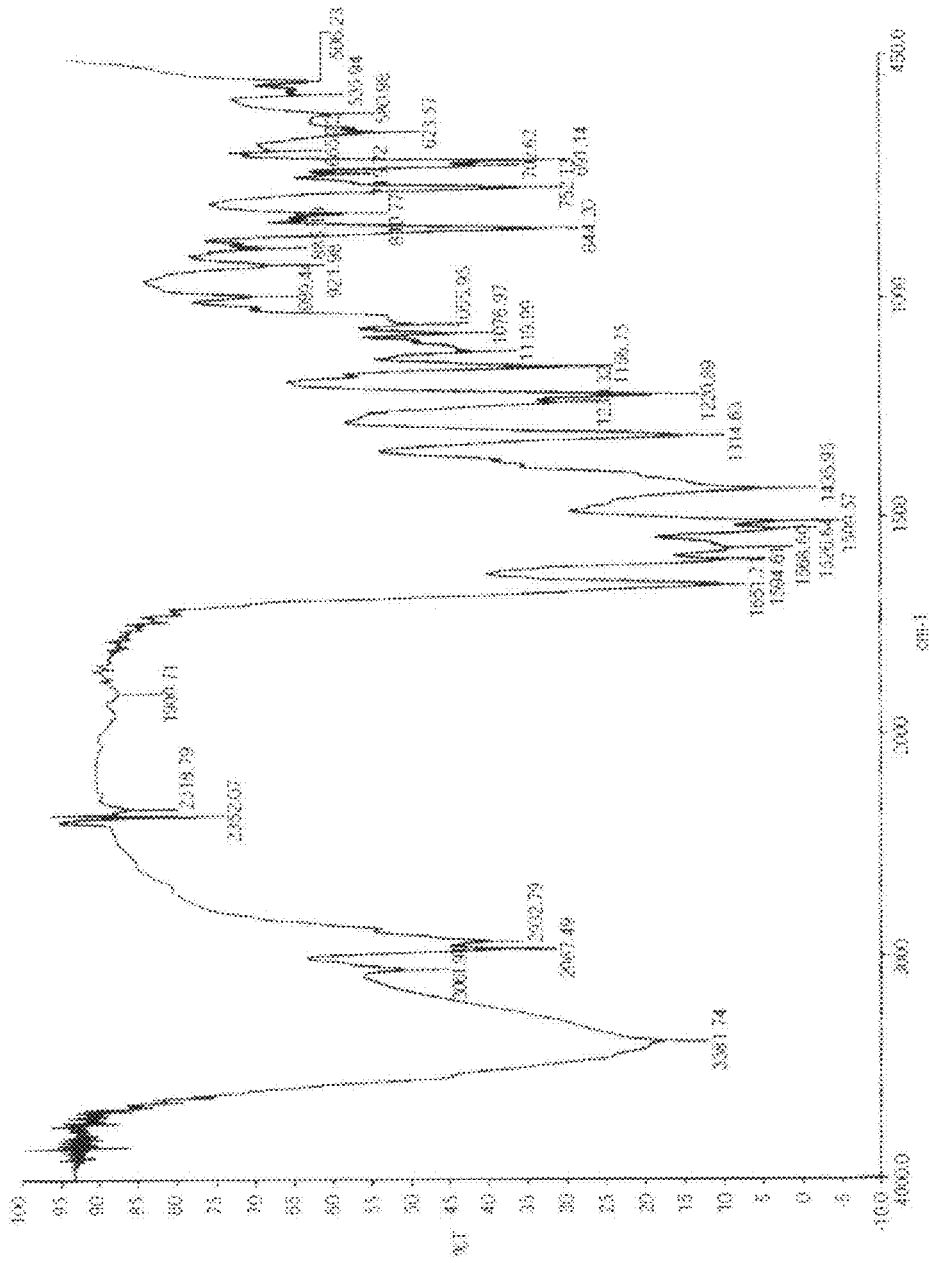
FIG. 16 shows an IR spectrum obtained from the product of Example 9.

Atorvastatin calcium (1 g) was dissolved in 2 mL of (S)-propylene glycol followed by the addition of 7 mL of isopropyl acetate and 1 mL of water. The resulting mixture was warmed to 55-60° C. and stirred for 8-10 hours to afford a translucent solution which was evaporated to give a gel-like residue which was further treated with 7 mL isopropyl acetate and heated to 55-60° C. for 8 hours, cooled to 20-25° C. and filtered and dried under vacuum at 50-60° C. to give 0.44 g atorvastatin calcium (S)-propylene glycol solvate. Propylene glycol content: 6.3% by NMR, KF=0.2%. The DSC and IR of this material are shown as FIGS. 15 and 16 respectively.

As many changes can be made to the examples which exemplify the invention without departing from the scope of the invention, it is intended that all matter contained herein be considered illustrative of the invention and not in a limiting sense.

The invention claimed is:

1. Crystalline atorvastatin calcium propylene glycol solvate prepared by a process comprising:
    (a) adding atorvastatin calcium to propylene glycol;
    (b) adding an organic co-solvent; and
    (c) isolating the solvate by filtration.

2. A process for the preparation of atorvastatin calcium comprising desolvating crystalline atorvastatin calcium propylene glycol solvate of claim 1 to produce atorvastatin calcium and propylene glycol.

3. The crystalline atorvastatin propylene glycol solvate of claim 1 wherein the process further comprises adding water after adding the organic co-solvent.

4. The crystalline atorvastatin propylene glycol solvate of claim 1 wherein the process further comprises drying the isolated solvate.

5. The crystalline atorvastatin calcium propylene glycol solvate of claim 1 wherein the molar ratio of atorvastatin calcium to propylene glycol is about 1:1.

6. The crystalline atorvastatin calcium propylene glycol solvate of claim 1 wherein the propylene glycol component has predominantly the (R) absolute configuration.

7. The crystalline atorvastatin calcium propylene glycol solvate of claim 1 wherein the propylene glycol component has predominantly the (S) absolute configuration.

8. The crystalline atorvastatin calcium propylene glycol solvate of claim 1 wherein the propylene glycol is present in any proportion of the (R) and (S) absolute configuration provided the proportion of the (R) and (S) propylene glycol is not about 1:1.

9. The crystalline atorvastatin calcium propylene glycol solvate of claim 1 having a DSC endotherm with a peak onset temperature of about 183° C. and a peak maximum of about 192° C.

10. The crystalline atorvastatin calcium propylene glycol solvate of claim 1 having a DSC thermogram as shown in FIG. 1.

11. The crystalline atorvastatin calcium propylene glycol solvate of claim 1 characterized by an IR spectrum (1% KBr) having characteristic peaks at about 3382, 1652, 1510, 1436, 1315, 1221, and 844 cm$^{-1}$.

12. The crystalline atorvastatin calcium propylene glycol solvate of claim 1 having an IR spectrum as shown in FIG. 2.

13. The crystalline atorvastatin calcium propylene glycol solvate of claim 1 wherein the organic co-solvent is selected from the group consisting of C3 to C5 alkyl esters and C3 to C6 alkyl ketones, and mixtures thereof.

14. The crystalline atorvastatin calcium propylene glycol solvate of claim 1 wherein the organic co-solvent comprises ethyl acetate and isopropyl acetate.

15. The crystalline atorvastatin calcium propylene glycol solvate of claim 1 wherein the organic co-solvent comprises methyl isobutyl ketone.

16. The crystalline atorvastatin calcium propylene glycol solvate of claim 3 wherein about 0 to about 2 volumes of water is added.

17. The crystalline atorvastatin calcium propylene glycol solvate of claim 1 wherein about 5 to about 9 volumes of organic co-solvent is added.

18. The crystalline atorvastatin calcium propylene glycol solvate of claim 1 wherein atorvastatin is added to about 5 to about 9 volumes of propylene glycol.

19. The crystalline atorvastatin calcium propylene glycol solvate of claim 1 wherein atorvastatin is added to about 0.5 to about 4 volumes of propylene glycol.

20. The crystalline atorvastatin calcium propylene glycol solvate of claim 1 wherein atorvastatin is added to R-propylene glycol.

21. The crystalline atorvastatin calcium propylene glycol solvate of claim 1 wherein atorvastatin is added to S-propylene glycol.

22. The crystalline atorvastatin calcium propylene glycol solvate of claim 1 wherein atorvastatin is added to a racemic mixture of the propylene glycol.

* * * * *